(12) United States Patent
Madin et al.

(10) Patent No.: US 8,366,656 B2
(45) Date of Patent: Feb. 5, 2013

(54) SYRINGE HAVING A RESILIENT PART IN ORDER TO FACILITATE AN INITIAL ASPIRATION

(75) Inventors: Graham John Madin, Mielkendorf (DE); Marc Andrew Koska, East Sussex (GB)

(73) Assignee: Star Syringe Limited, London (GB)

( * ) Notice: Subject to any disclaimer, the term of this patent is extended or adjusted under 35 U.S.C. 154(b) by 0 days.

(21) Appl. No.: 12/298,434

(22) PCT Filed: Oct. 3, 2006

(86) PCT No.: PCT/GB2006/003666
§ 371 (c)(1),
(2), (4) Date: Feb. 2, 2009

(87) PCT Pub. No.: WO2007/122363
PCT Pub. Date: Nov. 1, 2007

(65) Prior Publication Data
US 2009/0198194 A1    Aug. 6, 2009

(30) Foreign Application Priority Data

Apr. 25, 2006   (GB) .................................. 0608046.9

(51) Int. Cl.
*A61M 5/178*   (2006.01)
(52) U.S. Cl. ................ 604/36; 604/27; 604/35; 604/37; 604/38; 604/185; 604/212; 604/217; 604/218
(58) Field of Classification Search .............. 604/27, 604/35, 36, 37, 38, 118, 121, 122, 124, 125, 604/181, 182, 185, 187, 212, 214, 216, 217, 604/218, 900
See application file for complete search history.

(56) References Cited

U.S. PATENT DOCUMENTS

| 2,725,057 | A | 11/1955 | Lockhart |
| 4,463,880 | A | 8/1984 | Kramer et al. |
| 5,052,403 | A | 10/1991 | Haber et al. |
| 6,231,550 | B1 | 5/2001 | Laughlin |
| 2003/0187406 | A1 | 10/2003 | Spofforth |
| 2005/0209571 | A1 | 9/2005 | McKay |

FOREIGN PATENT DOCUMENTS

| EP | 1360969 A1 | 11/2003 |
| FR | 2659858 | 9/1991 |
| GB | 2368286 A | 5/2002 |
| JP | 1117349 | 8/1989 |
| JP | 2001187140 | 7/2001 |
| UA | 6385 | 5/2005 |
| WO | 97/41903 | 11/1997 |
| WO | 02/072182 | 9/2002 |
| WO | 2004/103429 | 12/2004 |
| WO | 2006/044010 | 4/2006 |

OTHER PUBLICATIONS

International Search Report and Written Opinion, International Application No. PCT/GB06/0366, mailed Jan. 2, 2007.

*Primary Examiner* — Bhisma Mehta
(74) *Attorney, Agent, or Firm* — Michael Best & Friedrich LLP

(57) ABSTRACT

A syringe comprises a barrel with a plunger in slidable and sealing engagement therein, and a needle attached to one end of the barrel. The barrel has an aspiration device in the form of manually-operable resilient portions, which can be operated to cause a pressure differential in the barrel, the pressure differential then being used to perform aspiration. The resilient portions are preferably formed by localized reductions of wall thickness in the external surface of the barrel.

25 Claims, 2 Drawing Sheets ent SYRINGE HAVING A RESILIENT PART IN ORDER TO FACILITATE AN INITIAL ASPIRATION This application is a U.S. national phase application filing of International Patent Application No. PCT/GB2006/003666, filed 3 Oct. 2006, which claims priority to British Patent Application No. 0608046.9, filed 25 Apr. 2006. The entire contents of each of the foregoing applications are incorporated herein by reference.

BACKGROUND OF THE INVENTION

I. Field of the Invention

This invention relates to a syringe having means to perform aspiration.

II. Description of Related Art

A conventional syringe has a barrel with a plunger in slidable and sealing engagement therein, and a needle attached to one end of the barrel. An injection using a conventional syringe is performed by inserting the needle of the syringe into a vial of injectant. The plunger of the syringe is then withdrawn while the user grips the barrel of the syringe with their other hand. This draws the injectant into the barrel of the syringe. The user may then check for any air bubbles in the injectant in the barrel, caused by air being inadvertently drawn into the barrel, and remove them in the usual way through the needle. The injection can then be performed.

The injection is administered by inserting the needle through the skin of a patient. It is necessary to check the position of the needle tip within the patient to ensure the injectant is delivered appropriately, such as to a muscle or into a blood vessel. This is achieved by aspiration of the syringe, which involves withdrawing the plunger a small amount once the needle is within the patient. This will cause the body material adjacent the needle tip to be drawn into the syringe barrel through the needle where the user can view it. Thus, if the injectant is intended for a blood vessel for example, if blood is drawn into the syringe then the needle tip is in the correct position for the injection to be delivered. If blood is not observed, the user would need to find an alternative injection site.

As can be appreciated, the aspiration procedure may be painful for the patient and also potentially hazardous. In particular, as the user is required to pull on the plunger while the needle is within a patient, this can cause unwanted movement of the needle tip, which may be painful. This is particularly so as, due to the seal the plunger needs to have with the barrel of the syringe, withdrawal of the plunger may require the application of a significant force thereby reducing the chance of keeping the syringe still. The position of the needle tip may also move during aspiration and therefore the injectant may not be delivered to the intended location. Thus, although the user may have thought that an appropriate injection site had been found by aspirating the syringe, the action of aspiration may cause the needle tip to move, which may render the injection ineffective or even dangerous to the health of the patient.

SUMMARY

According to the invention, we provide a syringe comprising a barrel having a plunger in slidable and sealing engagement therein, the barrel having aspiration means to allow aspiration of the syringe in use.

This is advantageous as by providing means to effect aspiration on the barrel, the syringe is easy to use and does not require withdrawal of the plunger. Thus, the user of the syringe can hold it by the barrel while they insert the needle in the patient and actuate the aspiration means with the same hand. This allows aspiration to be performed simply and with minimal movement of the syringe. This reduces the chance of pain to the patient and also helps ensure that the injectant is reliably delivered to the intended injection site.

The aspiration means may comprise manually-operable resilient means. Thus, the aspiration means can cause a pressure differential to occur in the barrel, which can be used to perform aspiration. Preferably, the aspiration means comprises at least one manually-operable resilient portion of the barrel. The user can easily apply finger pressure to the manually-operable resilient portion while holding the syringe and inserting the needle into the patient. By applying a squeezing pressure to the barrel, pressure is created within the barrel. Thus, when the user reduces the pressure applied to the manually-operable resilient portion, the pressure reduction experienced within the barrel draws in body material, such as blood, thereby effecting aspiration.

The barrel may have two manually-operable resilient portions. These are preferably diametrically opposed. As the resilient portions are diametrically opposed, both will naturally be gripped and thus squeezed by the user between finger and thumb. The grip required is consistent with current training of health care workers, and is often known as the 'pencil grip'. This makes the aspiration means particularly effective and easy to use.

Preferably the or each manually-operable resilient portion is formed by a localised reduction in wall thickness of the barrel. The reduction in wall thickness is preferably an external reduction, so as not to affect the seal of the plunger head against the internal surface of the barrel. The wall that forms the or each manually-operable resilient portion must be sufficiently thin to allow a user to easily squeeze the barrel to achieve a pressure change within the barrel. However, it must be thick enough to ensure the syringe barrel has sufficient structural integrity. For example, the hysteresis of the or each manually-operable resilient portion should be such that it does not affect the "feel" of performing the injection or reduce the quality of the seal between the barrel and a head of the plunger as it passes the manually-operable resilient portion or portions of the barrel. Preferably, the wall thickness of the resilient portion is substantially between 20% and 80% of the wall thickness of the remainder of the barrel. As can be appreciated this will depend on the barrel material and size of the syringe and may be 30%, 40%, 50%, 60% or 70% or any other appropriate amount in the range. In a standard syringe of polypropylene material with a wall thickness of 1 mm, the resilient portion will have a wall thickness of 0.8 mm. Preferably the barrel is of polypropylene, although it may be of ABS or polycarbonate.

A convex ridge may separate the reduced thickness wall portion from the normal thickness wall portion, in order to provide rigidity. The surface of the or each manually-operable resilient portion may be textured, to provide 'feel' for the user, as a physical indication of where to squeeze the barrel. The texture may be provided as a rough surface (as opposed to the smooth surface of the rest of the barrel) or as ridges on the surface. The ridges preferably extend axially.

Preferably, the or each manually-operable resilient portion has a width of between 10% and 40% of the circumference of the barrel and preferably substantially 25%. As can be appreciated the width of the or each resilient portion will depend at least the wall thickness of the resilient portion and material and size of the barrel and thus could be 15%, 20% or 30%. Further, the length of the or each manually-operable resilient portion may be between 20% and 80% and preferably between 40% and 60% of the longitudinal length of the barrel. However, as above, this depends on at least the wall thickness of the resilient portion and material and size of the barrel.

BRIEF DESCRIPTION OF THE DRAWINGS

There now follows by way of example only a detailed description of the present invention with reference to the accompanying drawings in which.

DETAILED DESCRIPTION

Figure 1:
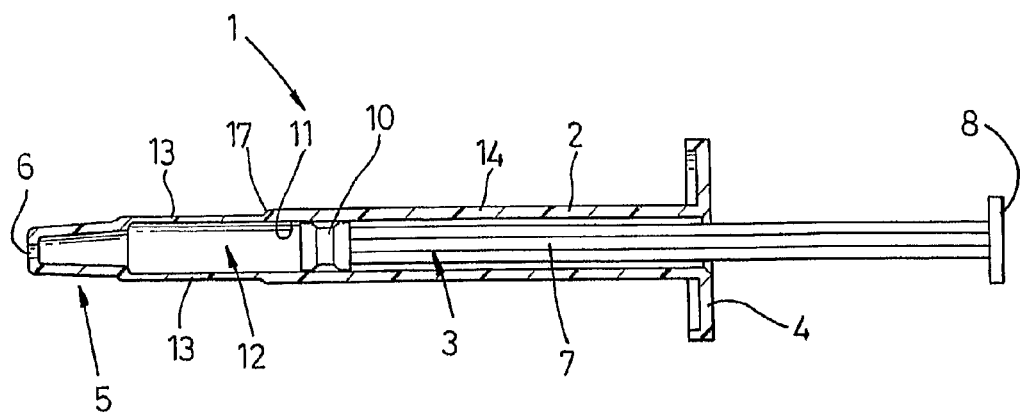
FIG. 1 shows a cross-section through a syringe in accordance with the invention.
Figure 2:
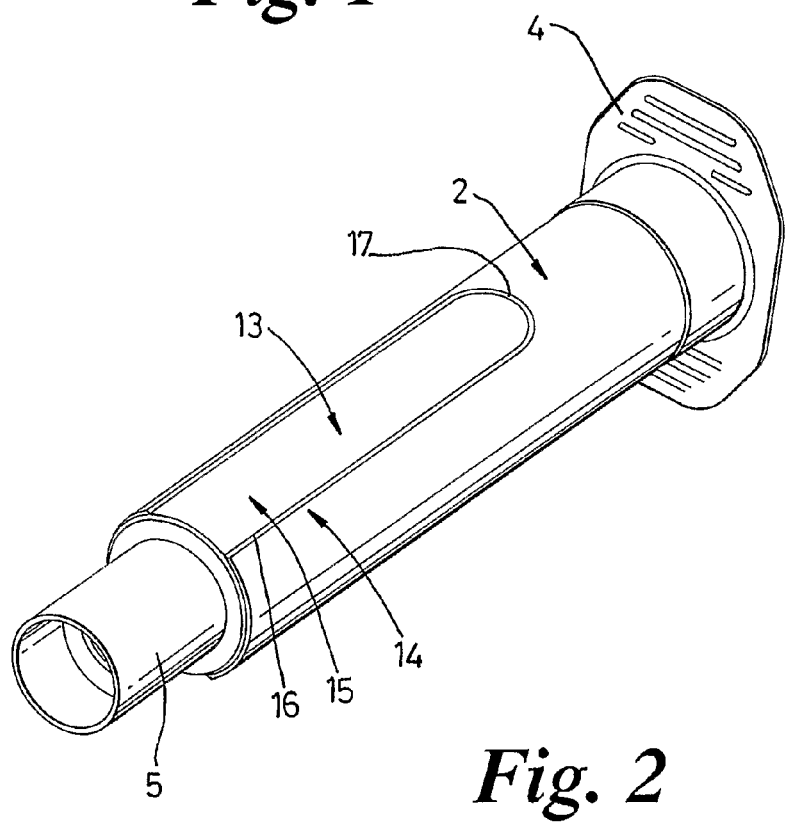
FIG. 2 shows a perspective view of the barrel of a syringe in accordance with the invention.

FIG. 1 of the drawings shows an injection device commonly known as a syringe 1. The syringe 1 comprises a barrel 2 and a plunger 3. The barrel 2 has an open proximal end provided with a gripping flange 4 and a distal end 5 having a liquid outlet 6. The liquid outlet 6 can be arranged in a variety of ways as needed to attach a needle; in FIG. 1 the needle would be affixed permanently by glue, heat or some other means. A luer slip design, as shown in FIG. 2, could also be used. The syringe plunger 3 comprises a rod 7 and a finger plate 8, for gripping the plunger. At the distal end of the rod is a plunger head of reduced diameter, carrying an elastomeric seal 10, which forms a seal with the inside surface 11 of the barrel 2 and defines a chamber 12 to receive injectant (not shown).

The barrel 2 is shown in more detail in FIG. 2. The barrel 2 includes a single wall having aspiration means comprising two diametrically opposed manually-operable resilient portions 13 (only one of which is visible in FIG. 2). The manually-operable resilient portions 13 are formed by a portion of the barrel wall of reduced thickness defined by a recess. The reduction of the wall thickness is on the external surface of the single wall of the barrel 2. Thus, the single wall of the barrel 2 includes an external surface that comprises a normal thickness part 14 and two reduced thickness parts 15 defining a recess in the external surface, each forming a manually-operable resilient portion, parts 14 and 15 being separated by a slightly convex ridge 16 bridging between the normal wall thickness and the reduced wall thickness, to provide rigidity. Each reduced thickness part 15 is substantially rectangular, and extends from the distal end 5 toward the proximal end of the barrel 2, where it terminates in an arcuate part 17.

The normal thickness part 14 has a thickness of approximately 1 mm. Each reduced thickness part 15 has a thickness of approximately 0.8 mm. However, depending on the size of the syringe 1, the normal thickness part 14 may be between 0.5 mm and 3 mm. Accordingly, each reduced thickness part 15 may be between 0.5 mm and 1 mm, such as 0.6, 0.7, 0.8 or 0.9 mm.

Each reduced thickness part 15 has a width of approximately 25% of the barrel circumference. This may be varied between 10% and 40% depending on the thickness and material and size of the barrel. The length of each reduced thickness part 15 again depends on the thickness and material and size of the barrel, but will normally be between 20% and 80%.

The gripping flange 4 may be formed integrally with the single wall and has a pair of diametrically opposed wings enabling the barrel 2 to be gripped between adjacent fingers in use. The portions 13 are formed in line with the wings, so that they do not interfere with the volume markings (not shown) on the barrel 2. These markings are always between the wings.

The portions 13 shown in FIG. 2 have a smooth external surface. In a modification (not shown) the external surface of the portions 13 may be textured, to provide a physical indication for the user of where they are. The textured surface may be roughened (in comparison with the smooth external surface of the remainder of the barrel) or be provided by ridges extending axially.

Figure 3:
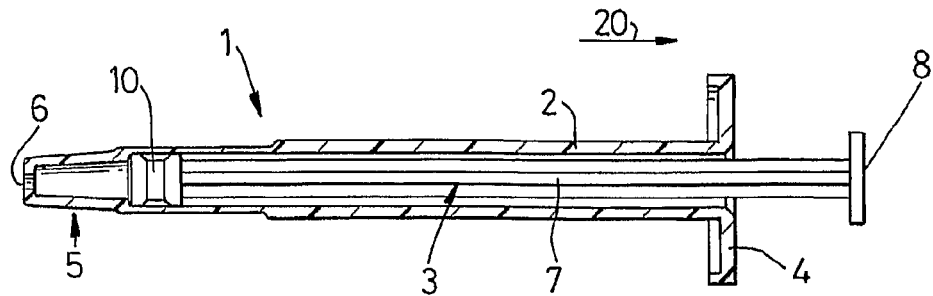
FIGS. 3 to 6 show an embodiment of the invention at different stages of operation.

The operation of the syringe 1 is illustrated in FIGS. 3 to 6. FIG. 3 shows the syringe 1 in a state where it is about to draw injectant into the barrel 2. Thus, having the needle (not shown) in a vial (not shown) of injectant, the plunger 3 is withdrawn in the direction of arrow 20 to draw the injectant into the chamber 12 of barrel 2.

Figure 4:
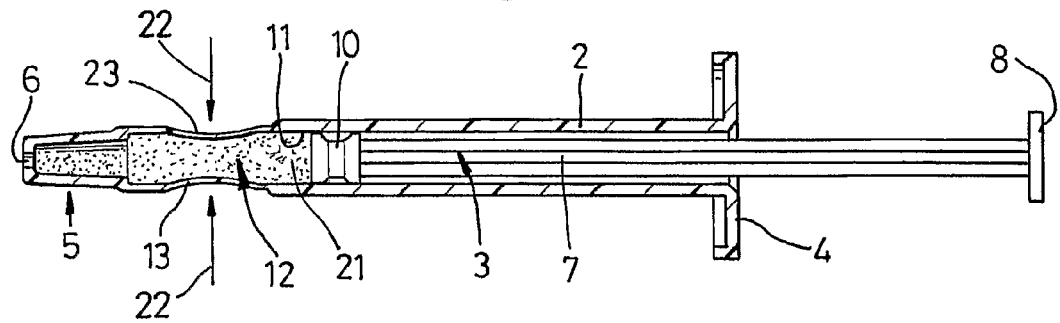
Figure 5:
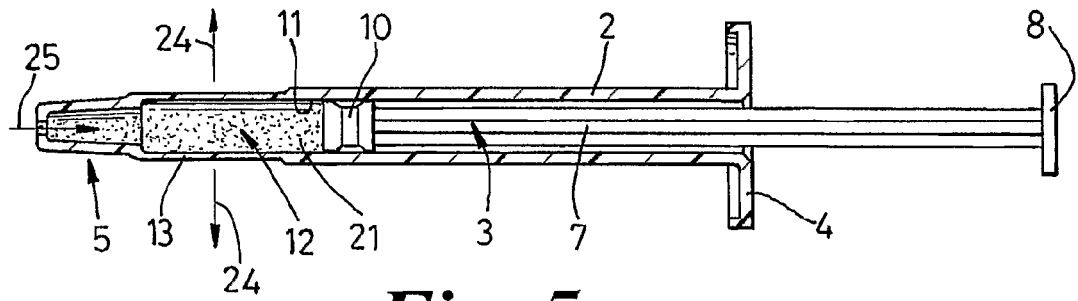

FIG. 4 shows the plunger 3 withdrawn and the chamber filled with injectant 21. It will be appreciated that more or less injectant can be withdrawn into the chamber 12, according to the amount required. Pressure substantially in the direction of arrows 22 can then be applied to the manually-operable resilient portions 13 as the user grips the single wall of the syringe barrel 2. As can be seen from FIG. 4, the manually-operable resilient portions 13 are resiliently deformed such that the volume of chamber 12 is slightly reduced. The deformation 23 of manually-operable resilient portions 13 is exaggerated for clarity. The needle of the syringe 1 may have been inserted into a patient before pressure is applied to the manually-operable resilient portions 13.

If not inserted already, the needle (not shown) of the syringe 1 is then inserted into a patient. To perform aspiration the user simply has to reduce the gripping pressure applied to the manually-operable resilient portions 13. Accordingly, the manually-operable resilient portions 13 will resile back to their original form as represented by arrows 24 and shown in FIG. 5. This causes the volume of chamber 12 to increase, creating a negative pressure in the barrel 2 that draws body material through the needle (not shown) and into the chamber 12, as represented by arrow 25. It will be appreciated that as all the user has to do is reduce the pressure of their grip on the barrel 2 to perform aspiration, the needle will remain steady and the injection can be performed accurately, reliably and safely.

Figure 6:
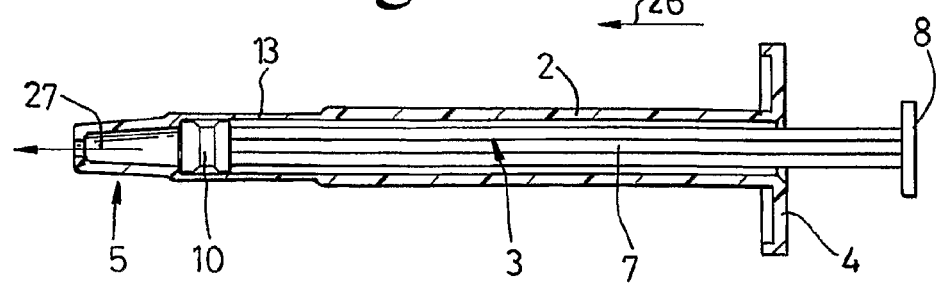

Finally, FIG. 6 shows the syringe 1 once the plunger has been pressed in the direction of arrow 26 to urge the injectant 21 out of the barrel 2, as shown by arrow 27, thereby delivering the injectant into the patient's body. The seal 10 is not impeded by the reduced thickness parts 15 as the wall thickness is reduced externally. The distal end of the plunger 3 may be in slidable and sealing engagement with the internal surface at a distal region of the barrel 2 during the injection and the aspiration.

The invention claimed is:

1. A syringe comprising a barrel and a plunger, said barrel including a single wall defining an internal surface, said plunger configured to perform an injection, a distal end of said plunger being in slidable and sealing engagement with said internal surface at a distal region of the barrel during the injection and aspiration, said wall having aspiration means to allow the aspiration of said syringe in use, said aspiration means comprising at least one manually-operable resilient portion formed by a localised reduction in thickness of said wall.

2. A syringe as claimed in claim 1, wherein said single wall has two manually-operable resilient portions.

3. A syringe as claimed in claim 2, wherein said two manually-operable resilient portions are diametrically opposed.

4. A syringe as claimed in claim 1, wherein said single wall defines an external surface, and wherein said localised reduction in thickness of said single wall is defined by a recess formed in said external surface.

5. A syringe as claimed in claim 1, wherein said localised reduction is substantially between 20% and 80% of the thickness of the remainder of said wall.

6. A syringe as claimed in claim 1, wherein said at least one manually-operable resilient portion has a width of between 10% and 40% of the circumference of said barrel.

7. A syringe as claimed in claim 6, wherein said at least one manually-operable resilient portion has a width of substantially 25% of the circumference of said barrel.

8. A syringe as claimed in claim 1, wherein a length of said at least one manually-operable resilient portion is between 20% and 80% of the longitudinal length of said barrel.

9. A syringe as claimed in claim 8, wherein said length of said at least one manually-operable resilient portion is between 40% and 60% of said longitudinal length of said barrel.

10. A syringe as claimed in claim 1, wherein a convex ridge separates a portion of the wall including the localised reduction from a remainder of said wall having a normal wall thickness.

11. A syringe as claimed in claim 1, wherein said at least one manually-operable resilient portion has a textured external surface.

12. A syringe as claimed in claim 1, wherein said plunger cooperates with said single wall of the barrel to define a chamber.

13. A syringe comprising:
   a barrel defined by a single wall, the wall defining an internal surface and a manually-operable resilient portion formed by a localised reduction in wall thickness for manual aspiration of the syringe; and
   a plunger configured to perform an injection, a distal end of said plunger being in slidable and sealing engagement with the internal surface at a distal region of the barrel during the injection and the aspiration and cooperating with the single wall to define a chamber.

14. The syringe of claim 13, further comprising a gripping flange on a proximal end of the barrel and formed integrally with the single wall.

15. The syringe of claim 13, wherein the single wall defines an external surface, and wherein the localised reduction in wall thickness is defined by a recess formed in the external surface.

16. The syringe of claim 13, wherein the single wall defines two manually-operable resilient portions formed by localised reductions in wall thickness on an external surface of the wall.

17. The syringe of claim 16, wherein the two manually-operable resilient portions are diametrically opposed.

18. A syringe comprising a barrel and a plunger, said plunger configured to perform an injection, a distal end of said plunger being in slidable and sealing engagement with an internal surface of said barrel at a distal region of said barrel during the injection and aspiration, said barrel having a single barrel wall, said wall having at least one manually-operable resilient portion formed by a localised reduction in wall thickness for the aspiration of said syringe.

19. The syringe of claim 18, wherein said single barrel wall defines said internal surface.

20. The syringe of claim 19, wherein said plunger cooperates with said single barrel wall to define a chamber.

21. The syringe of claim 18, wherein said single barrel wall defines an external surface, and wherein said localised reduction in thickness is on said external surface of said barrel wall.

22. The syringe of claim 21, wherein said localised reduction in thickness is defined by a recess formed in said external surface of said single barrel wall.

23. The syringe of claim 18, further comprising a gripping flange on a proximal end of said barrel and formed integrally with said single barrel wall.

24. The syringe of claim 18, wherein said barrel wall defines two manually-operable resilient portions formed by localised reductions in wall thickness on an external surface of the wall.

25. The syringe of claim 24, wherein said two manually-operable resilient portions are diametrically opposed.

\* \* \* \* \*

UNITED STATES PATENT AND TRADEMARK OFFICE
CERTIFICATE OF CORRECTION

PATENT NO. : 8,366,656 B2  Page 1 of 1
APPLICATION NO. : 12/298434
DATED : February 5, 2013
INVENTOR(S) : Madin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 81 days.

Signed and Sealed this
First Day of September, 2015

Michelle K. Lee
*Director of the United States Patent and Trademark Office*